United States Patent [19]
Alexander

[11] Patent Number: 5,827,199
[45] Date of Patent: Oct. 27, 1998

[54] BIOPSY PUNCH APPARATUS

[76] Inventor: A. Melvin Alexander, 1 E. Chase St. #1010, Baltimore, Md. 21202

[21] Appl. No.: 668,776

[22] Filed: Jun. 24, 1996

[51] Int. Cl.$^6$ ................................................. A61B 10/00
[52] U.S. Cl. .............................. 600/564; 606/1; 606/167; 606/184; 606/185; 600/562
[58] Field of Search .................................. 128/753, 751, 128/752, 754, 749; 606/1, 167, 172, 184, 185; 600/564, 565, 566, 567, 562

[56] References Cited

U.S. PATENT DOCUMENTS

| | | |
|---|---|---|
| 4,487,209 | 12/1984 | Mehl . |
| 4,832,045 | 5/1989 | Goldberger . |
| 4,926,877 | 5/1990 | Bookwalter . |
| 5,123,907 | 6/1992 | Romaine . |
| 5,183,053 | 2/1993 | Yeh et al. . |
| 5,325,857 | 7/1994 | Nabai et al. . |

Primary Examiner—Robert A. Hafer
Assistant Examiner—Justine R. Yu

[57] ABSTRACT

A biopsy punch apparatus includes a hollow handle that has an open handle top and an open handle bottom. A ring-like finger rest is attached to the hollow handle such that the finger rest projects outwardly from the hollow handle. An inwardly tapering, hollow transition member has a top end and a bottom end, and the top end is connected to the open handle bottom. The bottom end of the transition member extends away from the hollow handle. A circular cutting blade is connected to the bottom end of the transition member. The cutting blade has a cutting edge. The cutting edge includes a bevelled cutting edge which tapers from inside to outside the cutting blade. An outside surface of the hollow handle includes ridges and valleys for providing an increase coefficient of friction between a practitioner's fingers and the hollow handle. When the practitioner takes a biopsy sample, the practitioner can look down inside the hollow handle, can see the patient's tissue to be biopsy, and can see the biopsy sample as it is being cut.

2 Claims, 3 Drawing Sheets

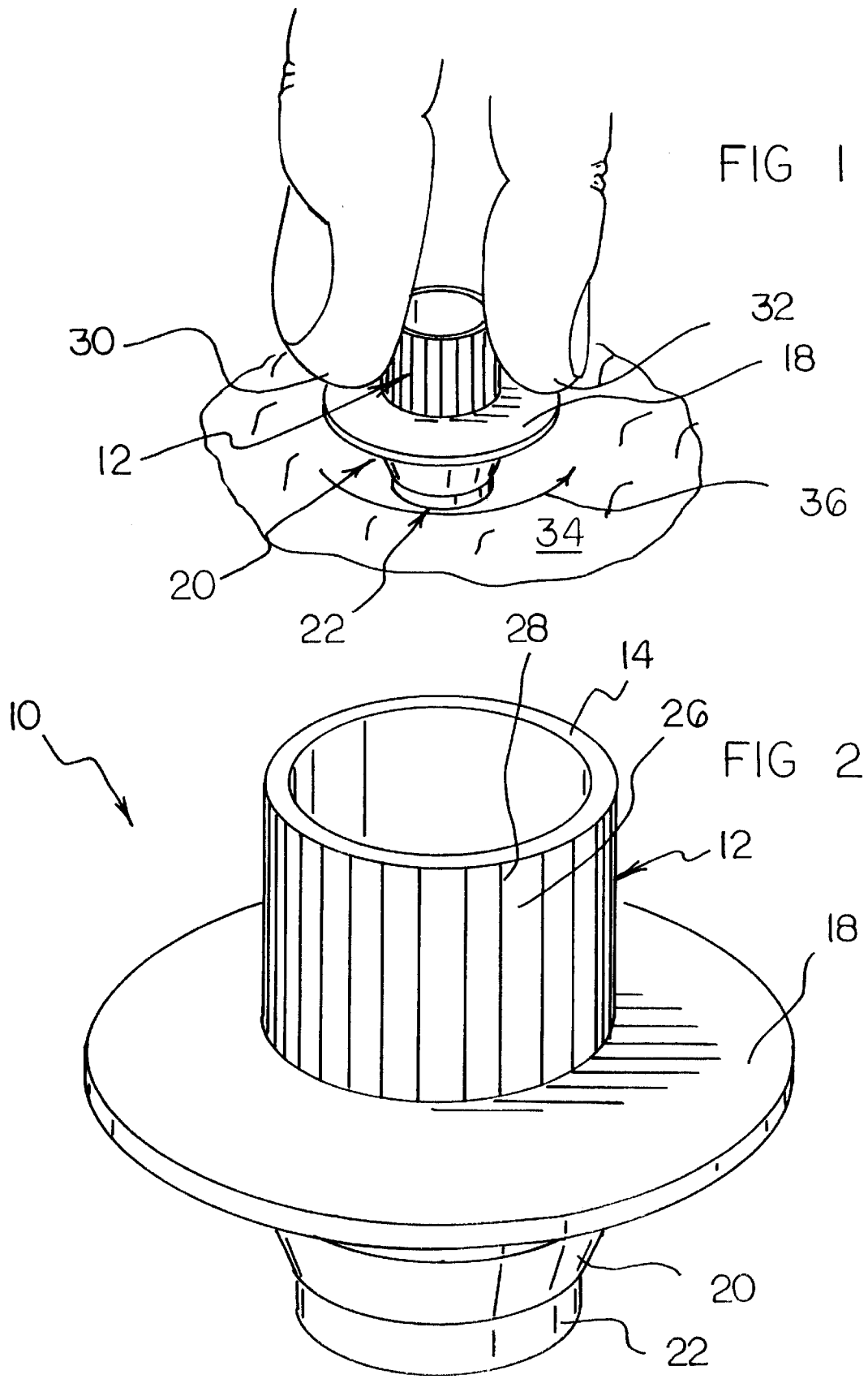

BIOPSY PUNCH APPARATUS

BACKGROUND OF THE INVENTION

1. Field of the Invention

The present invention relates generally to cutting devices and, more particularly, to cutting devices especially adapted for taking biopsies.

2. Description of the Prior Art

In the practice of medicine, biopsies are often taken. In taking a biopsy, tissue is cut off of a portion of a person's body, and the tissue is analyzed in some fashion. Throughout the years, a number of innovations have been developed relating to taking biopsies, and the following U.S. patents are representative of some of those innovations: U.S. Pat. Nos. 4,487,209, 4,832,045, 4,926,877, 5,123,907, 5,183,053, and 5,325,857. More specifically, each of U.S. Pat. Nos. 4,487,209, 4,926,877, 5,123,907, and 5,325,857 discloses a hollow needle used in taking biopsies. One problem associated with a biopsy needle is that the biopsy taken has a relatively small diameter. There are some biopsies, such as skin biopsies, which often need a biopsy that has a relatively large diameter. In this respect, it would be desirable if a biopsy cutter were provided which does not employ a biopsy needle. Furthermore, it would be desirable if a biopsy device were provided that can take a biopsy that has a relatively large diameter. Another problem associated with using a biopsy needle is that a small sample is often difficult to remove from the needle because the small sample becomes trapped in the needle. To avoid this problem, it would be desirable if a biopsy device were provided from which a biopsy can be easily removed.

U.S. Pat. No. 4,832,045 discloses a biopsy instrument that employs four V-shaped cutters that provide eight separate and distinct cutting edges. To keep eight separate and distinct cutting edges sharpened and effective for cutting may be quite burdensome. In this respect, for purposes of simplicity and ease of sharpening, it would be desirable if a biopsy cutter were provided which includes only one cutting edge.

U.S. Pat. No. 5,123,907 discloses a device for retaining stretched skin in a stretched condition so that a biopsy cutter can be used to cut a skin biopsy. The device does not have a cutting blade itself.

U.S. Pat. No. 5,183,053 discloses an elliptical biopsy punch which has an elliptical cutting edge and an apparently solid handle for supporting the cutting edge. With this device, the practitioner taking the biopsy cannot look down into the instrument to see how the inside portion of the cutting edge is cutting the tissue. In this respect, it would be desirable if a biopsy cutter were provided which enables a practitioner to look down into the device to see how the inside edge of the cutting edge is cutting the tissue. Moreover, it is noted that with this device, the downward cutting force on the cutting edge is exerted either by friction between the practitioner's fingers or the direct downward force of the practitioner's palm on the top end of the handle. This device does not provide for direct downward pressure of the practitioner's finger tips for exerting cutting pressure and control during the cutting operation. A person's finger tips are generally very sensitive, and, in this respect, it would be desirable if a biopsy cutter were provided which permits a practitioner's finger tips to exert direct downward pressure on the cutting edge of the device. Moreover, when a practitioner's fingers are prevented from slipping longitudinally merely by frictional contact between a handle and the practitioner's fingers, the practitioner's fingers may slip longitudinally if the handle becomes wet. In this respect, it would be desirable if a biopsy cutter were provided which helps prevent a practitioner's fingers from slipping longitudinally even when a handle becomes wet.

Thus, while the foregoing body of prior art indicates it to be well known to use biopsy punch devices, the prior art described above does not teach or suggest a biopsy punch apparatus which has the following combination of desirable features: (1) does not employ a biopsy needle; (2) can take a biopsy that has a relatively large diameter; (3) includes only one cutting edge; (4) enables a practitioner to look down into the device to see how the inside edge of the cutting blade is cutting the tissue; (5) permits a practitioner's finger tips to exert direct downward pressure on the cutting edge of the device; (6) provides a biopsy device from which a biopsy sample can easily be removed; (7) helps prevent a practitioner's fingers from slipping longitudinally even when the handle of the apparatus becomes wet; and (8) provides a specimen with only about one half to about three quarters turn of the apparatus, obviating the back and forth twisting movements required of prior art biopsy devices. The foregoing desired characteristics are provided by the unique biopsy punch apparatus of the present invention as will be made apparent from the following description thereof. Other advantages of the present invention over the prior art also will be rendered evident.

SUMMARY OF THE INVENTION

To achieve the foregoing and other advantages, the present invention, briefly described, provides a biopsy punch apparatus which includes a hollow handle that has an open handle top and an open handle bottom. A ring-like finger rest is attached to the hollow handle such that the finger rest projects outwardly from the hollow handle. An inwardly tapering, hollow transition member has a top end and a bottom end, and the top end is connected to the open handle bottom. The bottom end of the transition member extends away from the hollow handle. A circular cutting blade is connected to the bottom end of the transition member. The cutting blade has a cutting edge. The cutting edge includes a bevelled cutting edge which tapers from inside to outside the cutting blade. An outside surface of the hollow handle includes ridges and valleys for providing an increase coefficient of friction between a practitioner's fingers and the hollow handle. When the practitioner takes a biopsy sample, the practitioner can look down inside the hollow handle, can see the patient's tissue to be biopsied, and can see the biopsy sample as it is being cut.

The above brief description sets forth rather broadly the more important features of the present invention in order that the detailed description thereof that follows may be better understood, and in order that the present contributions to the art may be better appreciated. There are, of course, additional features of the invention that will be described hereinafter and which will be for the subject matter of the claims appended hereto.

In this respect, before explaining a preferred embodiment of the invention in detail, it is understood that the invention is not limited in its application to the details of the construction and to the arrangements of the components set forth in the following description or illustrated in the drawings. The invention is capable of other embodiments and of being practiced and carried out in various ways. Also, it is to be understood, that the phraseology and terminology employed herein are for the purpose of description and should not be regarded as limiting.

As such, those skilled in the art will appreciate that the conception, upon which disclosure is based, may readily be utilized as a basis for designing other structures, methods, and systems for carrying out the several purposes of the present invention. It is important, therefore, that the claims be regarded as including such equivalent constructions insofar as they do not depart from the spirit and scope of the present invention.

It is therefore an object of the present invention to provide a new and improved biopsy punch apparatus which has all of the advantages of the prior art and none of the disadvantages.

It is another object of the present invention to provide a new and improved biopsy punch apparatus which may be easily and efficiently manufactured and marketed.

It is a further object of the present invention to provide a new and improved biopsy punch apparatus which is of durable and reliable construction.

An even further object of the present invention is to provide a new and improved biopsy punch apparatus which is susceptible of a low cost of manufacture with regard to both materials and labor, and which accordingly is then susceptible of low prices of sale to the consuming public, thereby making such biopsy punch apparatus available to the buying public.

Still yet a further object of the present invention is to provide a new and improved biopsy punch apparatus which does not employ a biopsy needle.

Still another object of the present invention is to provide a new and improved biopsy punch apparatus that can take a biopsy that has a relatively large diameter.

Yet another object of the present invention is to provide a new and improved biopsy punch apparatus which includes only one cutting edge.

Even another object of the present invention is to provide a new and improved biopsy punch apparatus that enables a practitioner to look down into the device to see how the inside edge of the cutting blade is cutting the tissue.

Still a further object of the present invention is to provide a new and improved biopsy punch apparatus which permits a practitioner's finger tips to exert direct downward pressure on the cutting edge of the device.

Yet another object of the present invention is to provide a new and improved biopsy punch apparatus that provides a biopsy device from which a biopsy sample can easily be removed.

Still another object of the present invention is to provide a new and improved biopsy punch apparatus which helps prevent a practitioner's fingers from slipping longitudinally even when the handle of the apparatus becomes wet.

Yet still another object of the present invention is to provide a new and improved biopsy punch apparatus which is effective to obtain a biopsy sample with only about one half to about three quarters turn of the apparatus.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

The invention will be better understood and the above objects as well as objects other than those set forth above will become more apparent after a study of the following detailed description thereof. Such description makes reference to the annexed drawing wherein:

FIG. 1 is a perspective view showing a preferred embodiment of the biopsy punch apparatus of the invention in use by a practitioner taking a biopsy sample of a patient.

FIG. 2 is an enlarged perspective view of the embodiment of the invention shown in FIG. 1 removed from the patient and the practitioner.

DESCRIPTION OF THE PREFERRED EMBODIMENT

With reference to the drawings, a new and improved biopsy punch apparatus embodying the principles and concepts of the present invention will be described.

Figure 3:
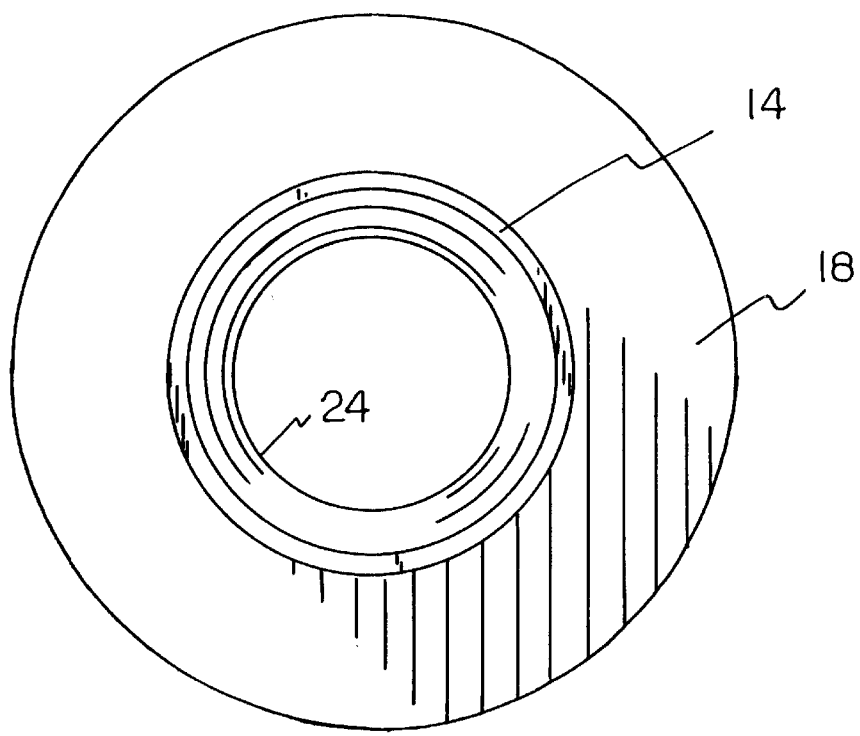
FIG. 3 is a top view of the embodiment of the invention shown in FIG. 2.
Figure 4:
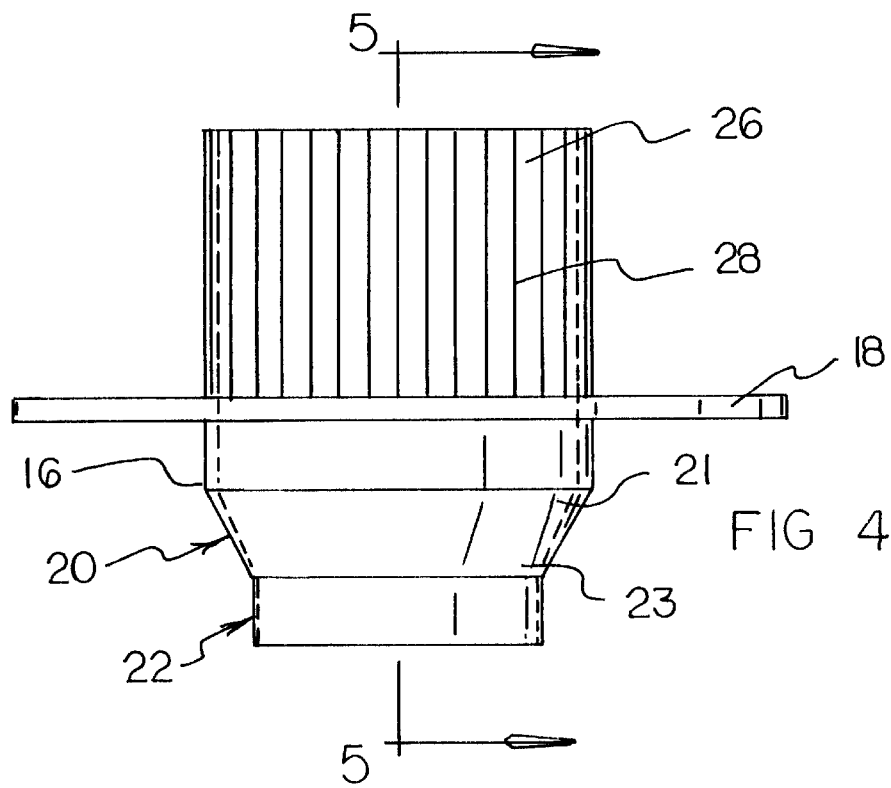
FIG. 4 is a side view of the embodiment of the invention shown in FIG. 3.
Figure 5:
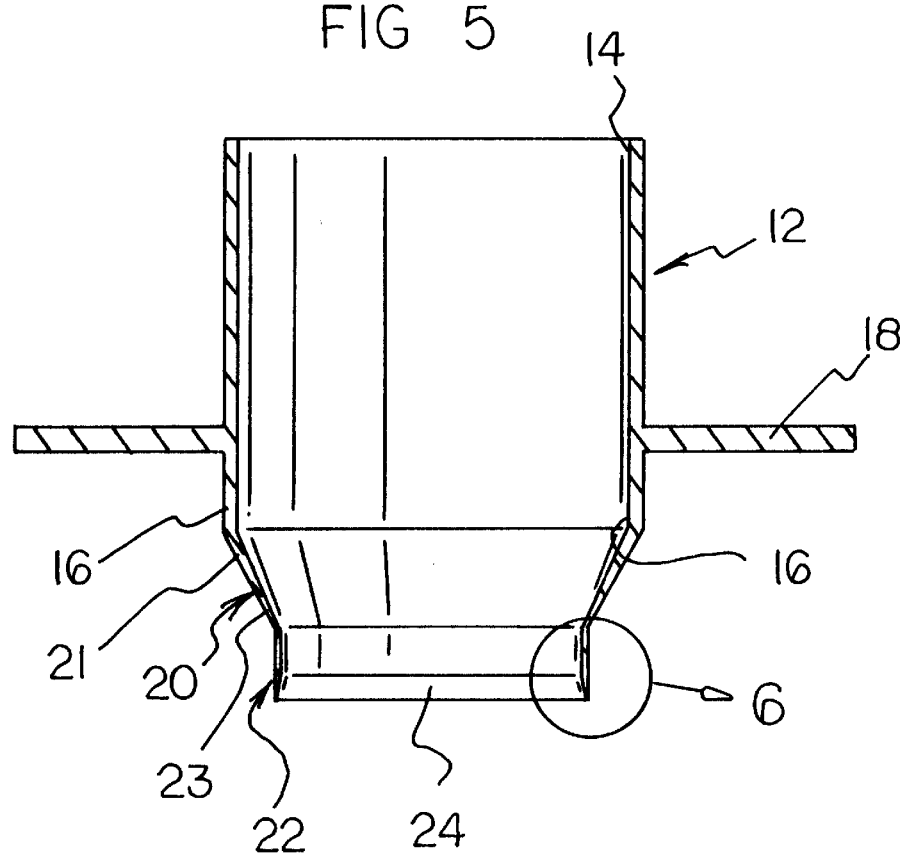
FIG. 5 is a cross-sectional view of the embodiment of the invention shown in FIG. 4 taken along line 5—5 thereof.
Figure 6:
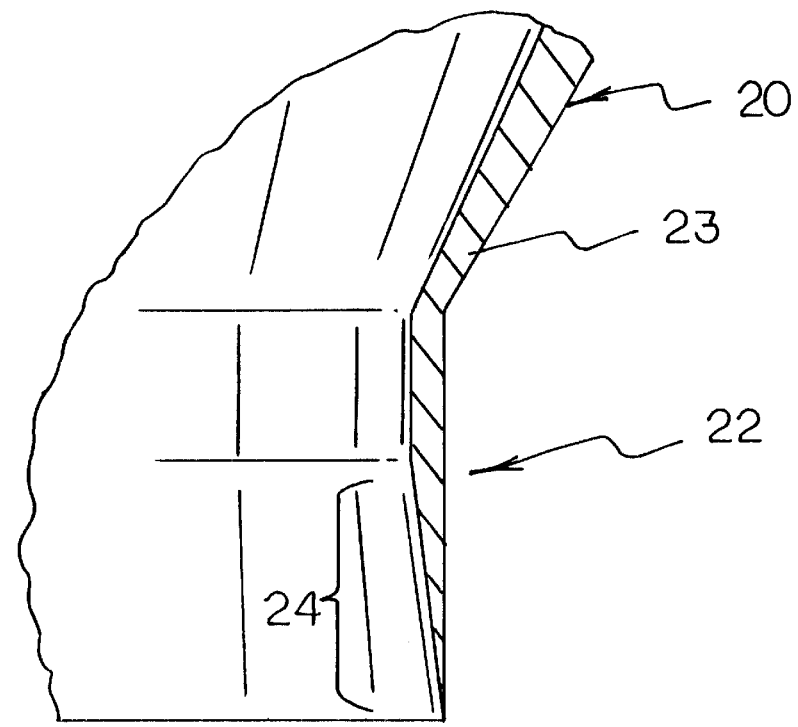
FIG. 6 is an enlarged cross-sectional view of the portion of the embodiment of the invention shown in the circled region 6 in FIG. 5.

Turning to FIGS. 1–6, there is shown an exemplary embodiment of the biopsy punch apparatus of the invention generally designated by reference numeral 10. In its preferred form, biopsy punch apparatus 10 includes a hollow handle 12 that has an open handle top 14 and an open handle bottom 16. A ring-like finger rest 18 is attached to the hollow handle 12 such that the finger rest 18 projects outwardly from the hollow handle 12. An inwardly tapering, hollow transition member 20 has a top end 21 and a bottom end 23, and the top end 21 is connected to the open handle bottom 16. The bottom end 23 of the transition member 20 extends away from the hollow handle 12. A circular cutting blade 22 is connected to the bottom end 23 of the transition member 20. The cutting blade 22 has a cutting edge 24. The cutting edge 24 includes a bevelled cutting edge 24 which tapers from inside to outside the cutting blade 22. An outside surface of the hollow handle 12 includes ridges 26 and valleys 28. The ridges 26 and valleys 28 provide a rough surface that increases the coefficient of friction between a practitioner's fingers and the outside surface of the hollow handle 12.

In using the biopsy punch apparatus 10 of the invention, a practitioner grasps the outside surface of the hollow handle 12 as shown in FIG. 1. The tip of the practitioner's thumb 30 and the tip of the practitioner's index finger 32 rest on the finger rest 18. By looking through the open handle top 14 and by looking outside the hollow handle 12, the practitioner places the cutting edge 24 on a patient's tissue, such as the skin surface 34 shown in FIG. 1. Then, the practitioner squeezes the hollow handle 12, pushes the thumb and index finger longitudinally down on the finger rest 18, and rotates the biopsy punch apparatus 10, such as indicated by arrow 36 in FIG. 6. As this is done, the cutting edge 24 makes a circular cut into the skin surface 34. All through the biopsy process, the practitioner is able to look both inside the hollow handle 12 and outside the hollow handle 12 to observe the progress of the biopsy process.

Under certain circumstances, a tissue that is cut by the cutting blade 22 may be pushed up into the transition member 20. When this occurs, the cut tissue may separate from the remainder of the tissue and may be temporarily trapped in the transition member 20. Then, when the biopsy punch apparatus 10 is lifted away from the patient, the biopsy sample is carried away from the patient by the biopsy punch apparatus 10. The biopsy sample can be readily removed from the biopsy punch apparatus 10 by either pushing the sample out of the apparatus or dumping the sample out of the apparatus.

The components of the biopsy punch apparatus of the invention can be made from inexpensive and durable metal and plastic materials. The biopsy punch apparatus can be made of materials that can withstand sterilization processes so that the biopsy punch apparatus can be used many times. Alternatively, the biopsy punch apparatus can be made as a single use, disposable device.

As to the manner of usage and operation of the instant invention, the same is apparent from the above disclosure, and accordingly, no further discussion relative to the manner of usage and operation need be provided.

It is apparent from the above that the present invention accomplishes all of the objects set forth by providing a new and improved biopsy punch apparatus that is low in cost, relatively simple in design and operation, and which may advantageously be used without using a biopsy needle. With the invention, a biopsy punch apparatus is provided which can take a biopsy sample that has a relatively large diameter. With the invention, a biopsy punch apparatus is provided which includes only one cutting edge. With the invention, a biopsy punch apparatus is provided which enables a practitioner to look down into the device to see how the inside edge of the cutting blade is cutting the tissue. With the invention, a biopsy punch apparatus is provided which permits a practitioner's finger tips to exert direct downward pressure on the cutting edge of the device. With the invention, a biopsy punch apparatus provides a biopsy device from which a biopsy sample can easily be removed. With the invention, a biopsy punch apparatus is provided which helps prevent a practitioner's fingers from slipping longitudinally even when the handle of the apparatus becomes wet. With the invention, a biopsy punch apparatus is provided which is effective to obtain a biopsy sample with only about one half to about three quarters turn of the apparatus.

Thus, while the present invention has been shown in the drawings and fully described above with particularity and detail in connection with what is presently deemed to be the most practical and preferred embodiment(s) of the invention, it will be apparent to those of ordinary skill in the art that many modifications thereof may be made without departing from the principles and concepts set forth herein, including, but not limited to, variations in size, materials, shape, form, function and manner of operation, assembly and use.

Hence, the proper scope of the present invention should be determined only by the broadest interpretation of the appended claims so as to encompass all such modifications as well as all relationships equivalent to those illustrated in the drawings and described in the specification.

Finally, it will be appreciated that the purpose of the foregoing Abstract provided at the beginning of this specification is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. Accordingly, the Abstract is neither intended to define the invention or the application, which only is measured by the claims, nor is it intended to be limiting as to the scope of the invention in any way.

What is claimed as being new and desired to be protected by Letters Patent of the United States is as follows:

1. A biopsy punch apparatus, comprising:

a hollow handle, the hollow handle being substantially cylindrical and being of a first diameter, the hollow handle having a handle top end and a handle bottom end;

a hollow transition member which has a transition member top end and a transition member bottom end, wherein the transition member top end is connected to the handle bottom end, the transition member bottom end extending away from the hollow handle and tapering to a second diameter at the transition member bottom end which is substantially less than the first diameter, the transition member bottom end being concentrically positioned relative to the handle bottom end;

a hollow cutting blade, the cutting blade being substantially cylindrical in shape, the cutting blade having a cutting blade top end spaced from a cutting blade bottom end, the cutting blade top end being connected to the transition member bottom end, with the cutting blade bottom end being shaped to define a cutting edge, the cutting blade top end and cutting blade bottom end both being of the second diameter, whereby the handle can be manually rotated to cause the cutting blade to cut tissue into a cylindrically-shaped section;

wherein there are no obstructions within an interior of the hollow handle, an interior of the hollow transition member and an interior of the hollow cutting blade, whereby the cutting edge of the cutting blade bottom end can be seen through the hollow handle and whereby the cutting blade can be engaged against tissue to cut a cylindrical sample of tissue which can pass freely through the hollow cutting blade, the hollow transition member and the hollow handle for removal from the handle top end of the hollow handle of the biopsy punch apparatus once a base of the cylindrical sample of tissue is separated from surrounding tissue.

2. The biopsy punch apparatus of claim 1, and further comprising a finger rest attached to said hollow handle, said finger rest being shaped to define a ring and projecting radially outwardly from the hollow handle.

* * * * *